(12) United States Patent
Pipeleers

(10) Patent No.: US 6,686,197 B2
(45) Date of Patent: Feb. 3, 2004

(54) METHOD FOR PRODUCING PREPARATIONS OF MATURE AND IMMATURE PANCREATIC ENDOCRINE CELLS, THE CELL PREPARATION AND ITS USE FOR TREATMENT OF DIABETES MELLITUS

(75) Inventor: Daniel Pipeleers, Roosdaal (BE)

(73) Assignee: Beta-Cell, N.V. (BE)

( * ) Notice: Subject to any disclaimer, the term of this patent is extended or adjusted under 35 U.S.C. 154(b) by 0 days.

(21) Appl. No.: 09/834,096

(22) Filed: Apr. 12, 2001

(65) Prior Publication Data

US 2002/0177228 A1 Nov. 28, 2002

(30) Foreign Application Priority Data

Apr. 12, 2000 (EP) .............................. 00201326

(51) Int. Cl.$^7$ ................................. C12N 5/00
(52) U.S. Cl. .................. 435/325; 435/366; 435/371
(58) Field of Search ................ 435/325, 366, 435/371

(56) References Cited

U.S. PATENT DOCUMENTS 5,050,612 A * 9/1991 Matsumura
5,858,973 A * 1/1999 Habener et al.
6,110,743 A * 8/2000 Levine et al.

OTHER PUBLICATIONS

Pipeleers, D.G. et al., "Transplantation of Purified Islet Cells in Diabetic Rats," *Diabetes*, vol. 40, No. 7, pp. 908–919, Jul. 1991.
Dawidson, I., "Purification of Single Pancreatic Endocrine Cells Using the Beckman JE–10X Elutriation Centrifuge," *Diabetes Research and Clinical Practice*, No. Suppl. 1, pp. S124–S125, 1985.
Beattie, G.M. et al., "Transplantation of Human Fetal Pancreas: Fresh vs. Cultured Fetal Islets of ICCS," *Journal of Molecular Medicine*, vol. 70, No. 1, pp. 70–73, 1999.
Korsgren, O. et al., "In Vitro Screening of Putative Compounds Inducing Fetal Porcine Pancreatic β–Cell Transplantation in Insulin–Dependent Diabetes Mellitus," *Upsala Journal of Medical Sciences*, vol. 98, No. 1, pp. 39–52, 1993.

* cited by examiner

*Primary Examiner*—Leon B. Lankford, Jr.
(74) *Attorney, Agent, or Firm*—Webb, Ziesenheim Logsdon Orkin & Hanson, P.C.

(57) ABSTRACT

A method for preparing a preparation of mammalian pancreatic endocrine cells comprising the steps: dissociating intact pancreatic tissue into a cell suspension comprising single cells and cell aggregates; enriching said cell suspension with regard to the content in endocrine cells by separating single cells and cellular aggregates with size <100 $\mu$m; and removing contaminating non-endocrine cells by density centrifugation.

21 Claims, 7 Drawing Sheets

Figure 1:
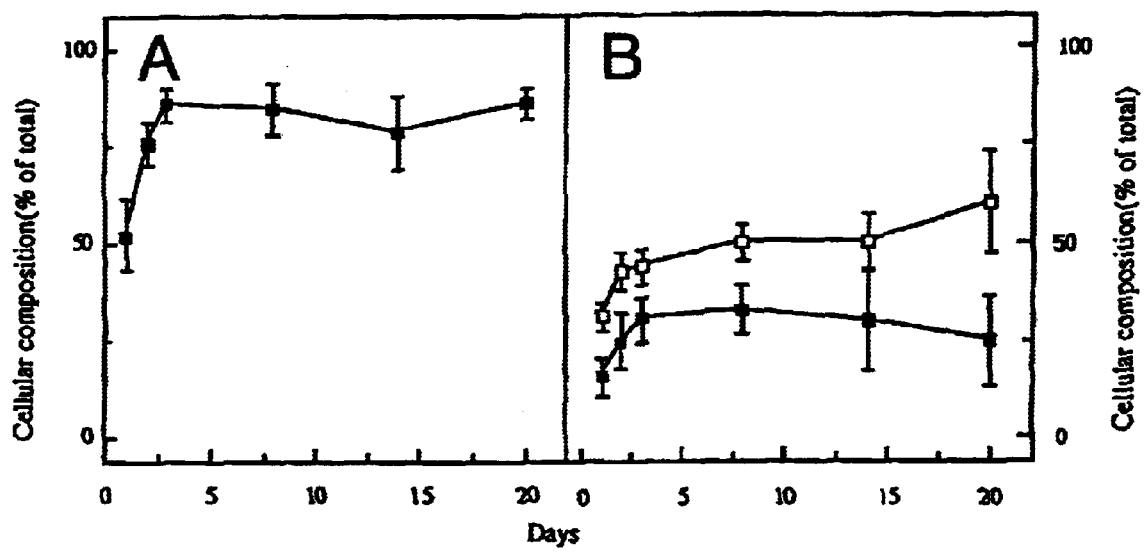

METHOD FOR PRODUCING PREPARATIONS OF MATURE AND IMMATURE PANCREATIC ENDOCRINE CELLS, THE CELL PREPARATION AND ITS USE FOR TREATMENT OF DIABETES MELLITUS

The present invention relates to a method for the large scale production of preparation of mature and immature pancreatic endocrine cells and their use for treatment of diabetes mellitus.

BACKGROUND TO THE INVENTION

Diabetes mellitus is defined as a chronic state of hyperglycaemia. This metabolic disturbance appears when insulin release has become insufficient, either as a result of a primary defect at the level of the insulin-producing beta cells or, secondary, when the beta cells fail to compensate for an increased peripheral resistance to insulin. The shift to elevated glucose levels can be counteracted by sustained adjustments in life style and by daily administration of hypoglycemic agents, under form of insulin injections or sulphonylurea tablets. Current treatment does however not succeed in a complete normalization of glucose homeostasis. Diabetic patients thus face the risk of developing chronic complications as a consequence of recurrent episodes of hyperglycemia. They are known to exhibit, as a group, a higher incidence of retinopathy and blindness, of nephropathy and renal failure, of neuropathy and amputations, of vasculopathy and cardiovascular disease. Diabetes is therefore considered as a major health problem. The disease is diagnosed in more than 5 percent of the Western population. Its impact on each patient's quality of life is variable but life-long (Report of the Expert Committee on the Diagnosis and Classification of Diabetes Mellitus, Diabetes Care 20,1183–1197, 1997).

A variety of stategies are currently explored in an attempt to find ways that stop the progression of the disease at any of its preclinical or clinical stages. Several are directed towards the pancreatic beta cells with the purpose of) reinstalling a functional beta cell mass that is sufficient to restore, at least in part, an endogenous control circuit in which insulin is released as a function of the metabolic needs. There are essentially two ways to achieve this goal. The first involves an implantation of foreign beta cells in order to replace the endogenous beta cell population or supplement it. It has been shown to correct the diabetic state in patients who had completely lost their endogenous beta cell mass (Warnock et al, Diabetologia 35:89–95, 1992; Ricordi et al, Transplantation 53;407–414, 1992; Gores et al, Lancet 341:19–21, 1993; Scharp et al, Transplantation 51:76–85, 1991). The second consists in administering drugs which increase the endogenous functional beta cell mass, either by inducing neoformation of beta cells, prolonging their survival or correcting their homeostatic function. Both strategies require the availability of large numbers of beta cells, either as cell grafts for implantation or as test model for screening and developing new drugs in the laboratory.

The number of patients who could benefit from a beta cell graft is, conservatively, estimated at 0.5 percent of the total population, which largely exceeds the number of candidates for other types of grafts. It is also clear that development of drugs acting on the beta cells involves extensive preclinical screening and testing for which large numbers of normal cells will be necessary. There is not yet a source of beta cells which can adequately fulfil both needs. Human pancreata have been used to produce beta cell preparations for transplantations as well as for in vitro studies but the number of donor organs is largely insufficient; moreover, criteria on human organ donation impede their use for drug development. These restrictions raise the need for producing beta cells from other species.

Among the larger mammals, pigs are considered as a potentially useful source of beta cell preparations since their use for medical applications faces fewer ethical obstacles than primates or other domestic animals, since pigs are relatively easy to breed and since porcine insulin is very similar to human insulin. Methods have been developed to isolate islet and tissue preparations from fetal, neonatal and adult pig pancreata. These preparations can normalize a diabetic state in immune-incompetent and in immune-competent mice (Korsgren et al, Surgery 113, 205–214, 1993; Korbutt et al, J Clin Invest 97, 2119–2129, 1996; Thomas et al, Transplantation 67:846–854, 1999; Lu et al, Xenotransplantation 5, 154–163, 1998). Fetal pig islet preparations have already been transplanted in diabetic patients, however without success (Groth et al, Lancet 344, 1402–1404, 1994). It is still unknown whether and if so, how successful xenotransplantation can be carried out in man. Use of reaggregated beta cell preparations with selected size and cellular composition might help a search for such conditions. Our studies in rodents have shown that purified islet endocrine cell aggregates exhibit a lower immunogenicity as allograft than intact islet tissue (Pipeleers et al, Diabetes 40, 908–919, 1991; Pipeleers et al, Diabetes 40, 920–930, 1991; Pipeleers-Marichal et al, Diabetes 40, 931–938, 1991, Pipeleers et al, Diabetologia 34,390–396, 1991). They also illustrate how variations in cellular composition influence the metabolic capacity of the grafts (Keymeulen et al, Diabetologia 40:1152–1158, 1997; Keymeulen et al, Diabetes 45,1814–1821, 1996). While these experiments demonstrated the usefulness of composing beta cell grafts in the laboratory, they did not offer an adequate methodology for clinical implantation. The methods that we used for composing the rat beta cell grafts do not allow large scale preparations of pancreatic endocrine cells. They involve prior isolation of the islets of Langerhans (herein defined as micro-organs with a diameter >100 μm containing a mixture of endocrine cell types including the insulin producing beta cells) and thus discard beta cells that are present as single cells or as small cell aggregates; the single beta cells are assumed to be adjacent to immature endocrine cells, i.e. cells which can differentiate into beta cells. As a result of this removal, little is known about these beta cells and the immature endocrine cells. Their relative proportion (with respect to the numbers incorporated in islets) is however not insignificant during early phases of life (In't Veld et al, Diabetologia 35:272–276,1992); in the human pancreas, they remain numerous throughout adult life (Bouwens and Pipeleers, Diabetologia 41:629–633, 1993). Since the migration and association of pancreatic endocrine cells into typical islet structures is considered as a step in maturation (Pictet and Rutter, development of the embryonic pancreas. In: Steiner D F, Freinkel N (eds) Handbook of Physiology, Section 7 Endocrinology Vol I: Endocrine Pancreas, Baltimore; Williams & Wilkins, 1972 pp25–66), the endocrine cells which do not occur in these micro-organs can be defined as "immature". Although the properties of immature beta cells and immature endocrine cells have not been well characterized, they are likely different from those of the "islets" which have matured under influence of their typical microanatomy and neighbouring endocrine cells (Orci and Unger, The Lancet 2;1243–1244,1975; Pipeleers, Experientia 440:1114–1126, 1984; Pipeleers, Diabetologia 30:277–291, 1987). The islet functions are considered as typical for mature beta cells; mature beta cells are larger than their immature counterparts (Pipeleers, unpublished observations). There is indirect evidence that the "immature" beta cells can achieve a growth of the beta cell mass. The loss of these cells during the isolation procedure is thus expected to result in a purified endocrine cell preparation which is only representative for the mature cell population, which contains only a subpopulation of the beta cells and which exhibits a low capacity for growth, three consequences that are disadvantageous when the isolated cells are to be used for the above-mentioned strategies, namely the construction of beta cell grafts and the development of drugs which aim to increase the functional beta cell mass.

In order to overcome said problems the invention provides a method according to claim 1. Preferred embodiments of the method according to the invention are described in subclaims 2 to 18. The preparations per se and heir use are subject of claims 19–22.

In the broadest aspect of the invention a method for the preparation of mammalian pancreatic endocrine cells is provided comprising the steps of dissociating intact pancreatic tissue into a cell suspension containing single cells and of enriching said cell suspension in immature and/or mature endocrine cells.

Intact pancreatic tissue is defined herein as the pancreatic organ or any of its segments after its dissection from the mammalian body.

A pancreatic endocrine cell is defined as a cell which is found in, or is isolated from, intact pancreatic issue and which expresses an endocrine marker, i.e. a molecule that has been identified in endocrine but not in exocrine cells. This marker can correspond to a constituent of an endocrine secretary vesicle or any other cell component.

Immature endocrine cells are defined by one or more of the following criteria: 1) a cellular phenotype that is characteristic for fetal endocrine cells but not for adult endocrine cells, for example the presence of gastrin immunoreactivity, or of synaptophysin immunoreactivity, without a positivity for any of the adult pancreatic hormones i.e. insulin, glucagon, somatostatin, pancreatic polypeptide. 2) occurrence in pancreatic tissue as unit of maximally four endocrine cells, 3) expression of a marker which is not found in homologous endocrine cells of adult pancreatic islets, such as cytokeratin 19 (CK19; human) or cytokeratin 7 (CK7; pig). Immature beta cells characteristically present a significantly smaller cell size when compared to adult beta cells (smaller than the mean diameter of adult beta cells minus three standard deviations) and a poor responsiveness to a maximal glucose stimulus (<3 fold stimulation of insulin release); the size these cells increases under maturation conditions.

Mature endocrine cells are defined by their location in pancreatic islets which are known to exhibit a typical vascularization (Bonner-Weir and Orci, Diabetes 31, 883–889, 1982; Pictet and Rutter, In: Steiner D F, Freinkel N (eds) Handbook of Physiology, Section 7 Endocrinology Vol I: Endocrine Pancreas, Baltimore: Williams & Wilkins, 1972 pp25–66).

Mature beta cells are characterized by their glucose-regulated biosynthesis and release of insulin, and their storage and release of insulin that is >90 percent processed into its mature form.

In contrast to previously described, and routinely used, methods for the isolation of pancreatic islets (Lacy P E and Kostianovsky M, Diabetes 16:35–39, 1967) the invention does not intend to isolate the "islets of Langerhans" under the form at which they occur in the intact pancreas. Instead, the whole pancreatic organ, including the "islets of Langerhans" is dissociated into single cells and small cellular aggregates before steps are taken to isolate the mature and immature endocrine cells.

By selecting the age of the pancreas, and the experimental conditions, the method can preferentially yield mature or immature endocrine cells or their subtypes. Thus, dissociation of late-fetal pig pancreata, elutriation of single cells from this dissociate, and culture of the elutriation fraction under specific conditions allows a large-scale purification of immature endocrine cells, both of the beta and alpha cell types. The invention describes the specific conditions under which this preparation can be used 1) to produce grafts with an important potential of beta cell growth in vivo, 2) to design and perform drug screening tests in vitro. In general, it provides the method for producing—from pancreata of different ages and species—endocrine cell preparations of selected cellular composition and properties for use as auto-, allo- and xenografts as well as for screening and assessing drugs in the laboratory.

DESCRIPTION OF THE INVENTION

I General Description of the Invention

This invention describes the production if preparations of mature and immature endocrine cells from the mammalian pancreas for use in the treatment of diabetes, more specifically the production of beta cell grafts with a growth potential, and the provision of experimental models in which drugs can be screened for their therapeutic effects on the functional beta cell mass.

The method can be used for a large scale production of endocrine cells from pancreata of various species, especially from late-gestation fetal pancreata and more specifically from fetal porcine pancreas, yielding preparations of defined size and cellular composition, selected purity in beta and alpha cells, predictable insulin biosynthetic capacity and ability of beta cell growth.

This particular application using late fetal porcine pancreas offers the following advantages in comparison to postnatal preparations from large species:
1. a lower risk of infection
2. higher purity in endocrine cells
3. larger endocrine cell number per technical procedure
4. distinct capacity for growth and longer survival of the beta cell mass
5. more reproducible functional properties In comparison to other methods for the isolation of fetal endocrine cells the method offers the following advantages:
1. higher purity in endocrine cells and their subtypes
2. larger endocrine cell number per organ
3. ability to select particular endocrine cell (sub) types and compose final preparations according to the metabolic needs.
4. availability of immature endocrine cells These properties make the method useful for 1) the preparation of cell grafts for transplantation in diabetic patients 2) the preparation of cell preparations or screening of drugs which regulate the functional beta cell mass.

II Detailed Description of the Invention

The most preferred embodiment of the method comprises six steps which, in combination, yield pancreatic endocrine cell preparations of selected size, composition and maturity;

1. dissociation to intact pancreatic tissue to the point where all tissue, including the islets of Langerhans, are preferably dispersed into cellular aggregates of <100 μm.
2. separation of the pancreatic dissociate according to particle size using counterflow centrifugation or elutriation to select single cells with size 6 to 15 μm (including immature endocrine cells) and small aggregates with size 15 to 100 μm (including mature endocrine cells).
3. elimination of non-endocrine or acinar cells from selected fractions by density gradient centrifugation.
4. enrichment in mature or immature endocrine cells by culture in specially formulated serum-free media.
5. purification of mature or immature endocrine, alpha or beta cells and their precursors by fluorescence-activated cell sorting.
6. composition of endocrine cell preparations with selected size, composition and maturity.

Steps 1 through 4 are used to purity mature and immature endocrine cells from 1 to 5 percent in intact tissue to a minimum of 60 percent and preferably 90 percent. Step 5 is necessary if a further purification is needed into (im) mature endocrine, alpha or beta cell enriched preparations. This procedure allows a large scale isolation of pancreatic endocrine cells while offering the possibility of selecting cells according to the experimental needs. A higher purity in intact endocrine cells is associated with a lower immunogenicity (Pipeleers et al, Diabetes 40, 920–930, 3991; Pipeleers-Marichal et al, Diabetes 40, 931–938, 1991; Pipeleers et al, Diabetologia 34; 390–396, 1991), inclusion of immature endocrine or beta cells is associated with a higher growth potential, addition of alpha cells increases and promotes the survival and function of beta cells (Pipeleers, Diabetologia 30, 277–291, 1987; Ling et al, Diabetologia 37, 15–21, 1994; Keymeulen et al, Diabetologia 40:1152–1158, 1997), standardized beta cell preparations are needed for standardized metabolic effects in diabetes (Keymeulen et al, Diabetologia 41:452–459, 1998), purified cell populations are required for drug testing (Pipeleers et al, Endocrinology 117:806–816, 1985; Gorus et al, Diabetes 37, 1090–1095, 1988).

Step 1

The preparation of pancreatic endocrine tissue is classically performed by collagenase digestion of the pancreatic gland and by separating a fraction enriched in islets of Langerhans using methods which isolate larger (>100 μm) tissue particles (by manual isolation under the dissection microscope) or particles with lower density (<1.07 g/ml). These fractions are enriched in islets of Langerhans and can be used to purify endocrine beta cells and alpha cells (Pipeleers et al, Endocrinology 117:806–816, 1985). These methods have the disadvantage that they result in the loss of (immature) endocrine cells that are contained in smaller tissue particles or/and in particles with higher density. This loss can be significant in quantitative and in qualitative terms as it will mean the loss of (immature) cells and small cell aggregates which are important for the growth of the beta cell mass. We have therefore chosen another methodologic strategy which starts with the dissociation of intact pancreatic tissue to the point, that all tissue, including the islets of Langerhans, is disassembled into particles <100 μm. These particles then form the basis for all subsequent processing steps.

Use of this stategy allows the isolation of larger numbers of endocrine cells, including immature endocrine and immature beta cells, than the classical. 'islet of Langerhans' based approach.

In step 1, the pancreatic tissue is mechanically dispersed during and following an incubation, first with collagenase for maximally 30 minutes and than with a calcium chelator EDTA (or EGTA) in a calcium-free medium containing DNase for maximally 30 minutes. The collagenase concentrations are determined per enzyme batch and set on the basis of, respectively, a disassembling of the intact tissue into particles with diameter <500, within 20 minutes, and maintaining this preparation free of strands and subsequent cell clumping. The calcium-free medium reduces cell adhesion and allows gentle dissociation of the endocrine tissue into single cells and small cellular aggregates. Immature endocrine cells will be present in particles smaller than 100 μm, and, in fetal pancreata, particularly as single cells with diameter 6–15 μm. Most mature endocrine cells will occur in particles with diameter 15–100 μm. Particles larger than 100 μm are removed by a 100 μm screen or by counterflow elutriation in which the smaller particles are collected at a flow rate of 225 ml/min and a rotor speed of 250 rpm (Beckman centrifuge J-6B, rotor JE10x).

Step 2

In this step single immature endocrine cells are separated from aggregated cells, including mature endocrine cells, while discarding debris. It is based on our finding that application of step 1 on fetal tissue results in release of immature endocrine cells as single units with a diameter of 6–15 μm. It is achieved by our adaptation of the technique of counterflow elutriation as to separate particles with diameter 6–15 μm from those with diameter 15–100 μm. The particle suspension is pumped at 25 ml/min into a Beckman (Palo Alto, Calif.) JE10x elutriator placed in a Beckman J6B centrifuge at 1500 rpm, whereby debris will be flushed cut and particles >6 μm are retained in the chamber. The pump speed will hen be increased to 190 ml/min in order to push the particles with diameter 6–15 μm out of the rotor chamber: this fraction is collected (<15 μm fraction) and contains the single immature endocrine cells. The speed of the centrifuge is then reduced to 0 rpm so that the content of the rotor can be collected as the 15–100 μm fraction. When applied on the <100 μm fraction of a dissociate from late-gestation fetal pig pancreata, all endocrine cells in the <15 μm fraction exhibit markers of immaturity (lack of typical glucose responsiveness, expression of duct cell marker CK7).

Step 3

The two fractions that are isolated after counterflow elutriation are contaminated by non-endocrine or acinar cells which exhibit a higher density (>1.070 g/ml) than endocrine cells. Density gradient centrifugation is used to reduce the level of contamination: the cell fractions from late-gestation fetal porcine pancreata are submitted to discontinuous Percoll gradients with densities of 1.040 g/ml and 1.075 g/ml. Endocrine-cell enriched preparations are collected at the interphase of density layers 1.40 and 1.075 g/ml; they yield preparations with >40 percent intact endocrine cells. The endocrine cells in the interphase from the 6–15 μm fraction are all immature; their number is consistently between 1 and 3 $10^7$ cells per fetal (porcine) pancreas.

Considering the mean number of fetuses (n=9) per sow—and hence per isolation experiment—, the yield in endocrine cells is minimally $10^8$ endocrine cells per isolation at a purity of >40%. The procedure therefore offers a large scale isolation of endocrine cells. This yield is higher than that from a human donor pancreas; it is also reproduced consistently.

At the end of step 3, the interphases also contain a proportion of non-granulated cells several of which are attached to endocrine cells. This non-granulated cell population—or a fraction thereoff—is to contributes to the growth of the beta cell mass through immature endocrine cells, i.e. cells which can which can differentiate into beta cells.

Step 4

The two fractions collected from step 3, namely interphase of <15 μm and interphase 15–100 μm, are further enriched in immature and mature endocrine cells by culture in specially formulated media:

for immature endocrine cells this medium is serum-free Ham's F10 with albumin (max 0.5%) as protein and supplements of nicotinamide (5 mM), glucocorticoids (max $10^{-6}$ M hydrocortisone), isobutylmethylxanthine (IBMX, 50 μM); compared to the media used for culture of islets of Langerhans this medium preserves the survival of immature endocrine cells and allows their increased storage of hormone during prolonged culture (2-fold increase in cellular insulin content after 4 weeks of culture); The degree of maturation and differentiation is suppressed by addition of serum and increasing the concentration of calcium to 2 mM; these latter supplements can be used to prepare fractions with more beta cell precursor cells.

for mature endocrine cells the culture medium is similar to that previously described for human beta cells (Ling and Pipeleers, J Clin Invest 98, 2805–2812, 1996), namely serum-free Ham's F10 with albumin (0.5%) and IBMX (50 μM).

After four days culture of the interphase <15 μm, the proportion of damaged cells is reproducibly under 10 percent, of intact endocrine cells above 70 percent, of non-granulated cells between 10 and 25 percent. The beta cells synthesize proinsulin at a rate of minimally 10 fmol/$10^3$ beta cells/hour. These quality control tests for cellular composition and functions are extended with microbiologic and toxicologic control tests.

For human implantation purposes the source animals are deprived from herds that are specific pathogen free according to the norms of the Federation of European Laboratory Animal Science Associations (FELASA) as defined this association (Laboratory Animals 32:1–17, 1998) and that comply with biological safety standards as proposed by the US Food and Drug Administration (Federal Register 49920–49932, August 1996).

The cell preparations described above can be used for transplantation and correction of diabetes in mice; they were shown to achieve growth of their beta cell mass (see example V). They can be used to purify composing cell (sub) types (step 5) and to design experimental models of single and aggregated cells with selected size, composition and maturity (step 6).

Step 5

The preparations obtained from step 4 can be dissociated into single cells using trypsin and DNase. The cell suspension is then submitted to fluorescence-activated cell sorting (FACS) using forward scatter (FSC), sidewards scatter (SSC) and fluorescence (FL) at 488 nm excitation and 520–540 nm emission as discrimination parameters. Populations of cell (sub) types are distinguished with respect to the location of intact non-granulated cells including immature endocrine cells (low FSC, low SSC, low FL); at higher SSC: enrichment in alpha cells; at higher FSC and FL: enrichment in beta cells whereby beta cell precursors and immature beta cells exhibit lower FSC and FL than mature beta cells.

Windows are set for the purification of these cell (sub) types as single cells.

Step 6

The cell (sub) types collected after step 5 can be cultured as single cells on polylysine-coated culture plates using the media defined in step 4 for immature or mature endocrine cells. The non-granulated cells with the immature endocrine cells (containing beta cell precursors) are cultured in the medium for immature endocrine cells 10 percent fetal serum.

The cells described under steps 4 and 5 can also be reaggregated into particles of selected size by gyratory shaking incubation in a $CO_2$ incubator using the media specified in the preceding paragraph and at cell densities from $10^4$ to $2.10^5$ per $cm^2$ surface of the bacteriologic dishes used for suspension culture. Cell aggregates of increasing size are obtained by increasing the cell density and increasing the speed and duration of gyratory shaking. Aggregates of varying composition can also be formed by mixing purified cell populations in varying proportions.

The preparations obtained by step 4 and 5 can be used for transplantation and for short- or long-term culture. They are useful in the treatment of diabetes, namely as a source of insulin in diabetic recipients and as an in vitro or in vivo model for drug screening.

The in vitro composed grafts and the cultured cell preparations can be submitted to functional analysis as well as to the microbiologic quality control tests that are required by regulatory authorities. The cell preparations can thus be screened for safety and efficacy while kept in culture and before actual implantation in diabetic patients.

EXAMPLES

Example I

Mass Isolation and Purification of Fetal Porcine Pancreatic Cells

Pregnant sows of 108 to 114 days of gestation were anaestethized and the fetuses removed surgically under sterile conditions in an operating theatre, the fetuses (crown-rump length 28±5 cm (mean±SD)) were decapitated and the pancreases removed by dissection under aseptic conditions and collected into sterile isolation medium (Pipeleers et al, Endocrinology 117:806–816, 1985). Over the past 100 dissections, a mean of nine fetuses were collected per pregnant sow. The tissue was cut with scissors into small fragments of approximately 1 $mm^3$ in size.

After washing the tissue fragments with isolation medium, the fragments were suspended in 200 ml isolation medium with 0.3 mg/ml collagense-P (Roche) (room temperature) and then shaken for 15 minutes. The tissue digest was filtered through a 500 μm filter and the filtrate centrifuged through a solution with density of 1.040 (6' at 1500 rpm) after which the pellet was saved. The material that was left on the 500 μm filter was again incubated with collagenase for another 15' and then filtered and centrifuged as before, whereby the pellet was again saved. The material that remained on the filter the second time was resuspended in a calcium-free dissociation medium (Pipeleers and Pipeleers-Marichal, Diabetologia 20:654–663, 1981) and dispersed during a 15 min incubation at room temp, before filtration and centrifugation as described above; this dissociation procedure was repeated on the material that was left on the filter.

The four pellet fractions were suspended in isolation medium containing 2% newborn calf serum (NCS), and filtered through a 100 μm filter to remove large cell clusters; the filtrate was now composed of single cells and small (<100 μm diameter) cellular aggregates. This cell suspension was pumped into the chamber of a JE-10X counterflow elutriation rotor (Beckman instruments Inc, Palo to Alto, Calif.) and centrifuged at 1500 rpm and a pump setting of 190 ml/min. Under these conditions, particles with a diameter of <15 μm were flushed out of the chamber, which thus retained particles with a larger size (15–100 μm). The elutriated fractions were centrifuged and the pellet resuspended in a medium with a density of 1.040 and layered on top of a medium with density 1.075; after centrifugation or 20 min at 2500 rpm, the interphase between 1.040 and 1.075 was removed with a siliconized Pasteur pipette and washed with isolation medium containing 2% NCS. The cells were counted in a Bürker counting chamber.

From the elutriated <15 μm fraction, between 30 and 50 million cells were obtained for each fetal pancreas. These cells were single (>60%); they were plated into 14 cm bacteriological petri dishes containing HAM's F10 with 110 mg/% glucose, penicillin 0.075 mg/ml, streptomycin 0.1 mg/ml, 2 mM glutamine, 2 mM $CaCl_2$, 50 μM Isobutylmethylxanthine (IBMX), 1 μM Hydrocortisone, 5 mM Nicotinamide and 0.5% Bovine Serum Albumin, with 0.5 to 1.0 million cells per ml medium. After 16 hrs culture at 37° C. and 5% CO2 in air, the cells were washed and the medium replaced by the same type HAM's F10 as before except for a lower calcium concentration (0.2 mM). Under these conditions, the cells were kept in suspension culture for up to 6 weeks. During culture the cells reaggregated spontaneously; the size of the aggregate was increased by increasing the cell density in the medium and by rotation.

During the first four days of culture, the total cell number decreased by 40%, mainly as a result of disintegration of damaged cells and acinar cells. The cell preparation was now composed of minimally 70 percent endocrine cells (with 30 to 50% insulin-containing beta cells, 15 to 45% glucagon-containing alpha cells, 5 to 10% somatostatin-containing D cells), of 10 to 25% non-granulated cells (i.e. cells that do not contain the typical endocrine secretory granules as seen in electron microscopy), <5% exocrine cells and <10% dead cells (FIG. 1). The insulin content of this cell preparation ranged it from 0.3 to 1.5 μg insulin/μgDNA and from 4 to 7 ng per thousand beta cells. This cellular insulin content is five-fold lower than in mature beta cells. The immaturity of the beta cells is also illustrated by their positivity for the ductal cell marker cytokeratin 7, and their poor secretory and biosynthetic responsiveness to glucose (less than 3-fold stimulation). This fraction is thus considered as containing immature beta cells. Other cells in this preparation are also immature as they all express the cytokeratin 7 marker; since they are also positive for synaptophysin they should be considered as belonging to the endocrine lineage. Since these cells do not present with the typical endocrine secretory vesicles, they should be considered to represent immature endocrine cells. Such immature endocrine cells are therefore precursors of immature beta cells which present the typical endocrine secretory vesicles in their cytoplasm.

When 10 percent fetal calf serum or swine serum was added the preparations maintained a higher proportion of non-granulated cells (up to 40%) for longer culture periods. These cells are positive for cytokeratin 7 and for synaptophysin and negative for carbonic anhydrase which suggests that this fraction contains endocrine precursor cells.

Figure 2:
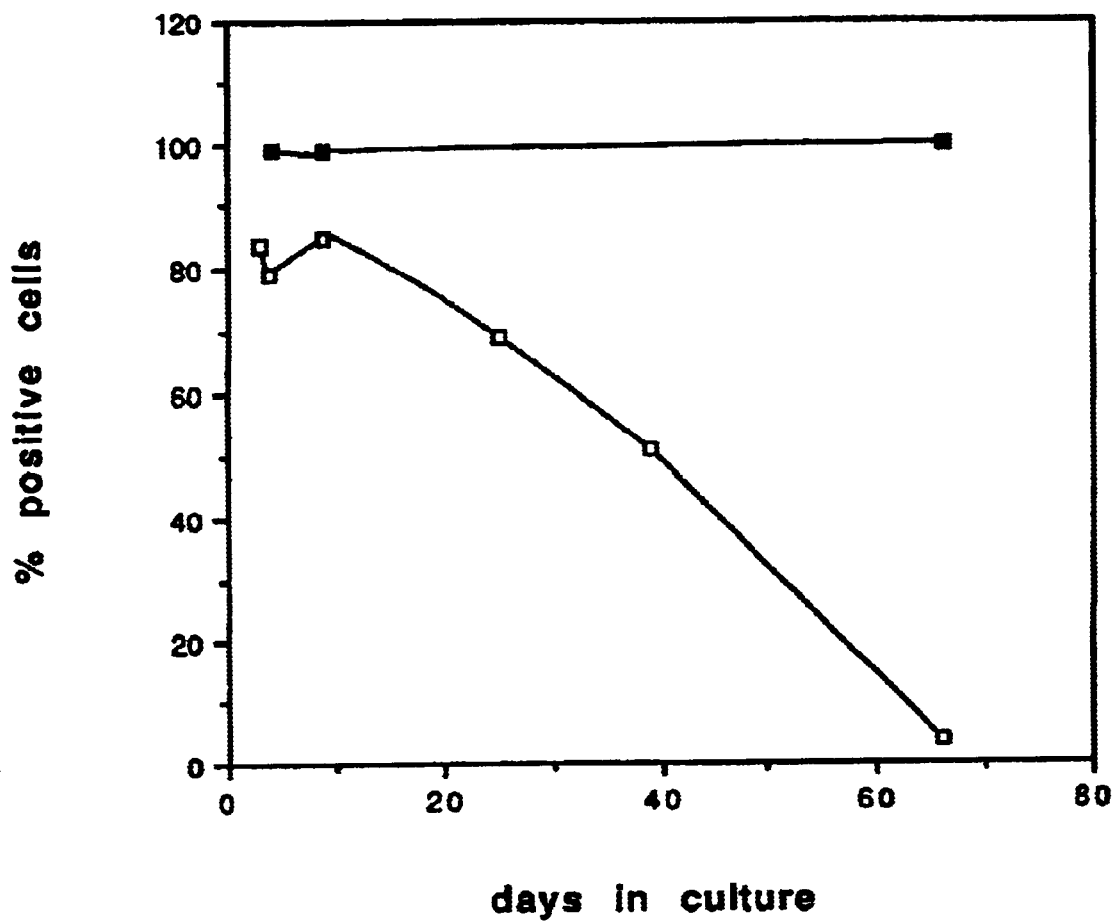

In serum-free medium, the preparation became entirely composed of endocrine cells, with a slight majority of insulin-containing cells (40 to 60%). Over a period of four to ten weeks, the size of the beta cells and their insulin content progressively increased. When nicotinamide and glucocorticoids were removed, the cells increased their glucose-responsiveness as judged by their insulin-secretory activity during perfusion at low (2.5 mM glucose) and higher (5–7.5–10 mM) glucose. This sign of functional maturation was accompanied by a loss of the cytokeratin 7 staining (FIG. 2). The immature endocrine cells can thus mature in vitro; they also mature in vivo following transplantation (see further).

From the elutriated 15–100 μm fraction, between 15 and 25 million cells were obtained for each fetal pancreas. This fraction is mostly composed of aggregated cells (less than 20% single cells) and thus contains mature endocrine cells. Culture, in medium without nicotinamide and glucocorticoids leads to a preparation of 60 to 80 percent aggregated endocrine cells with mature beta cells, and 20 to 30 percent non-granulated cells.

Example II

Use of fluorescence-activated cell sorting (FACS) to further enrich the preparations in immature or mature endocrine cells, in particular beta cells.

Figure 3A:
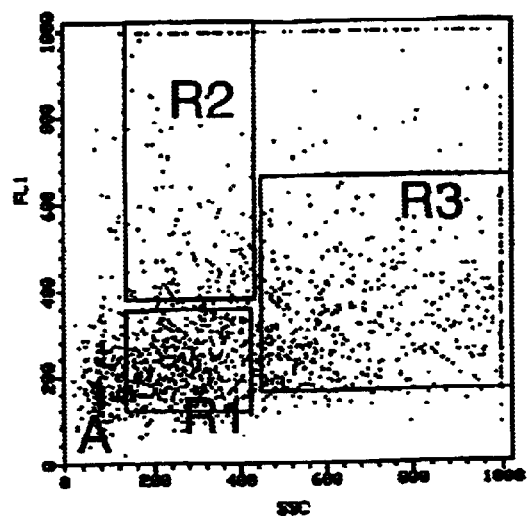
Figure 3B:
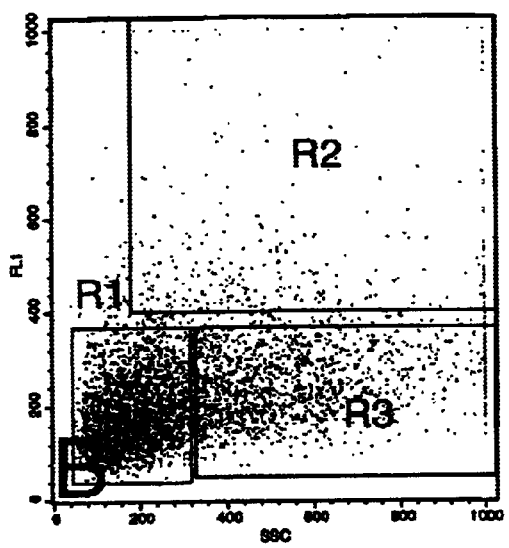
Figure 3C:
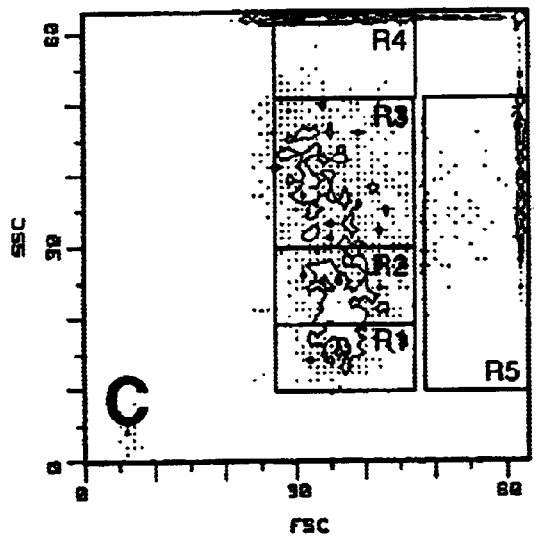

1) Purification of immature cell preparations which are predominantly composed of non-granulated cells and which contain immature endocrine cells.
   Starting preparation:
   elutriation-fraction 15 μm
   cultured for 4 days in HAM's F10 medium used for immature cells and supplemented with 2% newborn calf serum and $CaCl_2$ up to final 2 mM concentration.
   dissociated in calcium-free medium containing trypsin and DNase.
   composition: non-granulated cells >40%; endocrine cells 35–50%.
   FACS conditions:
   analysis for sidewards scatter (SSC) and for fluorescence at excitation 488 nm, emission 520–540 nm (FL1)
   Sorting of R1, R2 and R3 windows (FIG. 3a)
   cellular composition of the fractions obtained: R1+R2 contain >70% non-granulated cells, with a higher fluorescence in the R2 population as a marker for immature endocrine cells
   R3 contains >85% endocrine cells
2) Enrichment in immature beta cells
   Starting preparation:
   elutriation fraction <15 μm
   cultured for minimally seven days in HAM's F10 medium used for immature cells
   dissociation in calcium-free medium containing trypsin and DNase
   composition starting preparation before FACS: >70% endocrine cells.
   FACS conditions:
   analysis for sidewards scatter (SSC) and for fluorescence at excitation 488 nm, emission 520–540 nm (FL-1).
   sorting of R1, R2 and R3 windows (FIG. 3b)
   cellular composition of the fractions obtained:
   R1 contains >50% immature insulin-positive cells
   R2 contains >90% mature endocrine cells
   R3 contains >75% glucagon-positive cells
3) Purification of immature beta cells and of glucagon-containing cells:
   Starting preparation:
   elutriation fraction <15 μm
   cultured for minimally seven days in HAM's F10 medium used for immature cells.
   dissociation in calcium-free medium containing trypsin and DNase
   composition starting preparation before FACS: >75% endocrine cells.
   FACS conditions;

analysis for sidewards-scatter and forward scatter sorting of R1, R2, R3, R4, R5 windows (FIG. 3c)
cellular composition of the fractions obtained
  R1 contains >75% insulin-positive cells
  R3+R4 contain >90% glucagon-positive cells Example III Fetal pig derived beta cells produce insulin at rate that is comparable to that in adult human beta cells.

Figure 4:
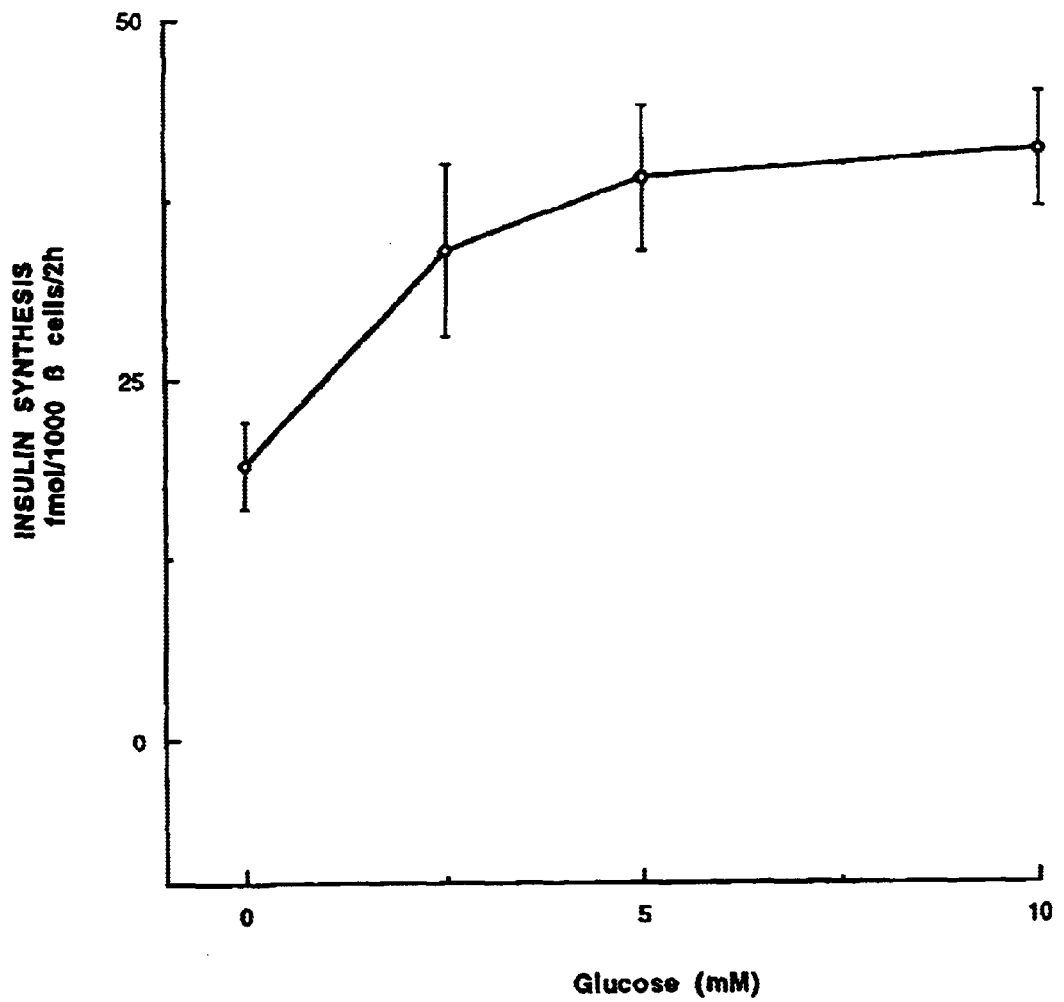

Endocrine cell preparations as obtained in example I are collected from the culture dishes and washed in isolation medium. A fluorescence toxicity assay (Hoorens et al, J Clin Invest 98, 1568–1574, 1996) indicates less than 15% dead cells. Samples of 25.000 to 75.000 cells are incubated in 500 µm HAM's F10 medium supplemented with 0.5% bovine serum albumin and 25 µCi $^3$H-tyrosine (5 µM final concentration). Labeling of newly synthesized proteins is conducted over 120 min at 37° C. and 95% $O_2$/5% $CO_2$ Total protein and proinsulin synthesis are measured as previously described (Ling and Pipeleers, Endocrinology 134, 2614–2621, 1994). Date are expressed per 1000 beta cells. At 10 mM glucose the rates of insulin biosynthesis (41±3 fmol per $10^3$ beta cells per 2 hrs) are comparable to those in adult human beta cells (37±8 fmol per $10^3$ beta cells per 2 hrs; p>0.05). At 0 mM glucose, the rates are lower in both species, but the decrease is only 50% in fetal beta cells (FIG. 4).

Example IV

Fetal pig beta cells resemble human beta cells—rather than rat beta cells—in their glucose metabolism, and, consequently, in subsequent glucose signaling.

Figure 5:
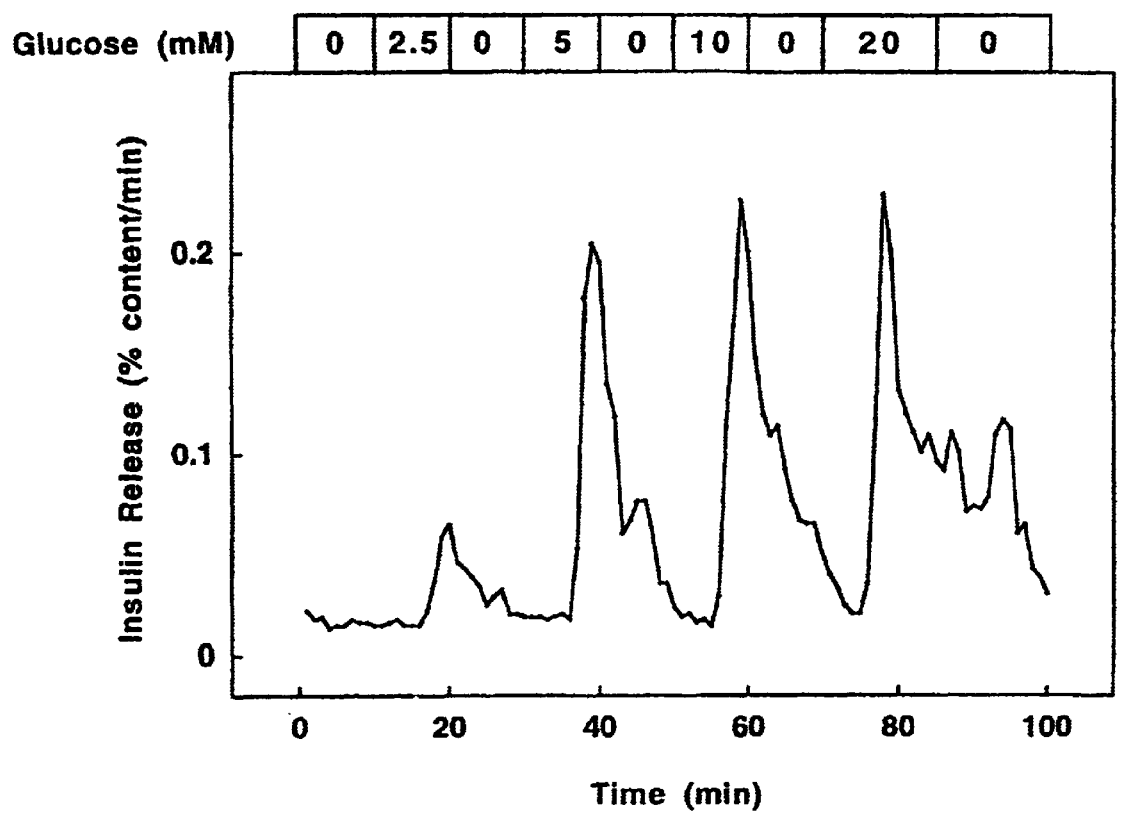

The rates of glucose utilization and oxidation were compared in isolated human (HP), fetal pig FP) and rat beta cell preparations which were incubated for 2 hrs with $^3$H and $^{14}$C-labelled glucose. These studies indicated a dose dependent increase in the rates of utilization and oxidation in the three species, but human and fetal pig preparations utilized 5 to 10-fold more glucose than rat beta cells (Table 1). The fetal beta cells exhibited the lowest rates of glucose oxidation which reached its maximum at 5 mM glucose; this range in dose-dependent oxidation corresponds with the range in dose-dependent insulin release and synthesis when fetal beta cells are exposed to glucose (FIG. 5).

Example V

Fetal Porcine Endocrine Cell Preparations are Able to Normalize Diabetes in Mice The cell preparations obtained as described under example I were reaggregated overnight by gyratory shaking incubation (Queu Orbital Shaker at 21 rpm) at 5%, $CO_2$ in air at 37° C. in 14 cm bacteriological petri dishes at a cell density of approx. $10^5$ cells/cm². The aggregates were implanted into immunodeficient nude mice that had been made diabetic by intravenous injection of 90 mg/kg body-weight of alloxan. Animals were anaesthetized with avertin and an incision was made in the dorso-lateral skin at the level of the kidney, the kidney was extruded and a small incision made in the kidney capsule; an obdurator was inserted between the kidney capsule and the kidney parenchyma and the capsule was carefully detached from the underlying tissue. The reaggregated porcine pancreatic cells were collected from their culture dish and brought into a small volume of HAMF10 containing 5% decomplemented mouse serum after which they were taken up in sterile thin plastic tubing blocked at the end by two metal surgical clamps, and subsequently centrifuged by hand for 2' at approximately 100 rpm. Immediately before implantation the tip of the tubing was cut and the pelleted material injected under the kidney capsule in the pocket prepared by the canulae. The opening in the kidney capsule was sutured using an electric low temperature cautery device and the kidney replaced into the body cavity after which the incision was closed with sutures. The animals were followed weekly by measuring their to fasting glycaemia on a drop of tail vein blood using glucometer and the graft was removed after 40 to 200 days and the insulin content measured.

The transplanted animals exhibited a normalization of their glycaemia levels 4 to 14 weeks after the implantation and remained normoglycaemic for more than 100 days (Table 2). This normalization was not due to remaining insulin in the pancreas, as extracted insulin levels in this organ were found to be <0.6 µg/organ (pancreatic insulin content of non-diabetic animals is 15–25 µg). The insulin content of the graft was 5 to 25 µg at the time of implantation and increased up to ten-fold during the 200 day follow-up period.

Figure 6:
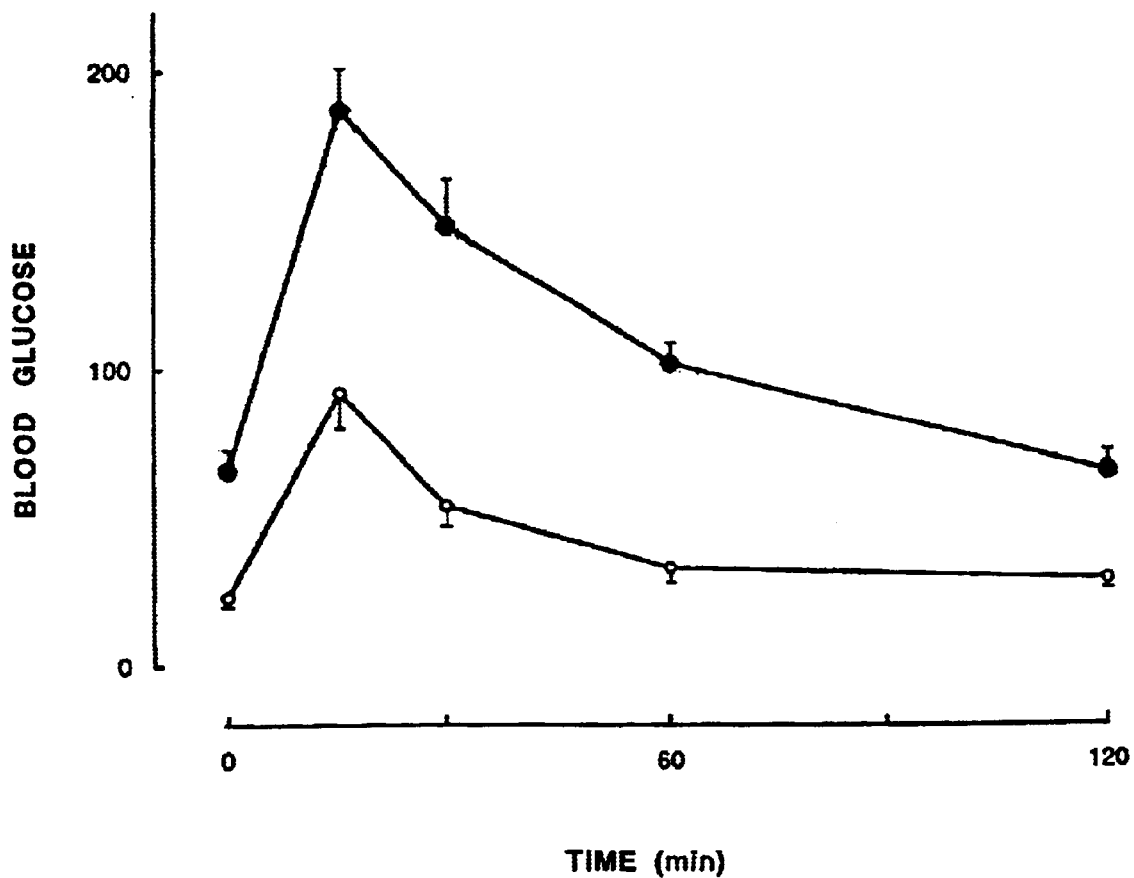

The rapidity of normalization varied with the number of implanted beta cells, taking 10 weeks for implants with 0.8 million beta cells, 8 weeks for 1.6 million beta cells and 4 weeks for 3 million beta cells. The beta cells mature after transplantation: they loose their positivity for cytokeratin 7 within 10 days. Their glucostat function maintains low glucose levels in the transplanted animal, even after oral glucose challenge (FIG. 6).

Figure 7:
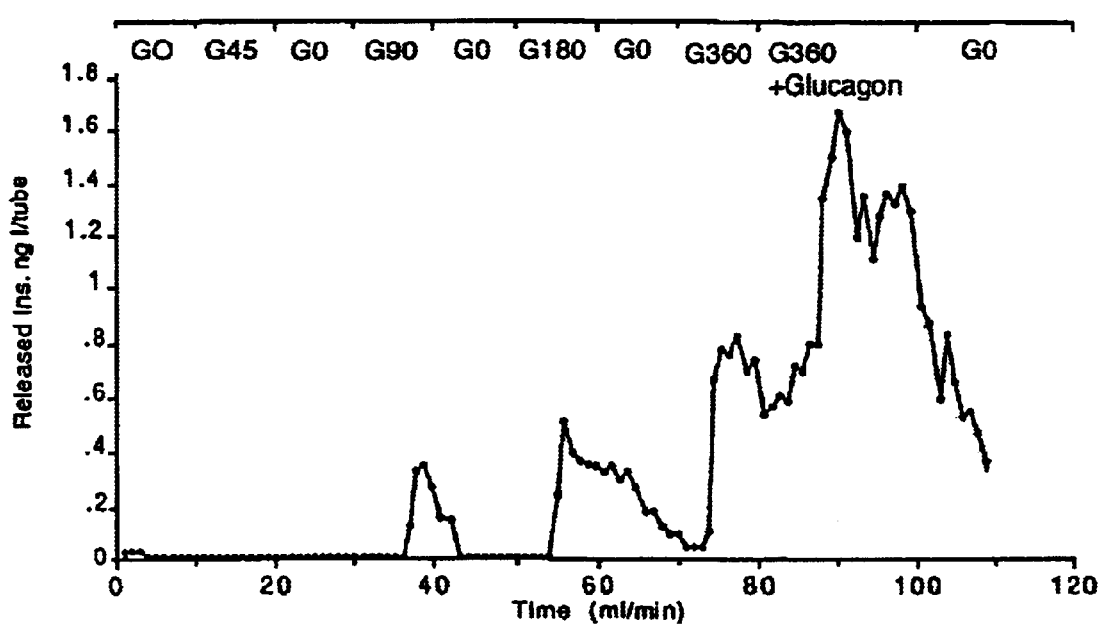

In vitro perfusion of a nu/nu mouse kidney containing a fetal pancreatic cell graft as described above showed that the beta cells in the kidney were responsive to glucose. In FIG. 7 the perfusion results are shown from a graft 112 days after implantation. A dose dependent insulin release response was observed that could be augmented with 10 mM glucagon.

TABLE 1 glucose utilization and glucose oxidation by fetal procine (FP), human (HP) and rat pancreatic endocrine cells.

| Glucose | Glucose utilization (pmol/1000 cells/2h) | | | Glucose oxidation (pmol/1000 cells/2h) | | | % oxid./util. | | |
|---|---|---|---|---|---|---|---|---|---|
| (mM) | HP-cell | FP-cell | rat B-cell | HP-cell | FP-cell | rat B-cell | HP-cell | FP-cell | rat B-cell |
| 1 | 75.3 | 28.4 | 2.6 | 9.6 | 4.3 | 1.8 | 13 | 15 | 69 |
| 2.5 | 108.2 | 57.8 | 7.4 | 14.1 | 8.5 | 4.8 | 13 | 15 | 65 |
| 5 | 126.7 | 104.4 | 12.3 | 20.4 | 14.5 | 9.0 | 16 | 14 | 73 |
| 10 | 178.2 | 175.0 | 25.9 | 28.8 | 18.4 | 21.6 | 16 | 11 | 83 |
| 20 | 203.8 | 252.4 | 43.8 | 31.1 | 19.0 | 28.6 | 15 | 8 | 71 |

TABLE 2

Effect of fetal pig islet cell implants in diabetic nude mice.

| | Plasma Glucose (mg %) | | | | | | |
|---|---|---|---|---|---|---|---|
| Posttransplantation week | 0 | 4 | 6 | 8 | 10 | 12 | 14 |
| Normal controls | 127 ± 7 | 132 ± 7 | 126 ± 10 | 126 ± 8 | 130 ± 6 | 119 ± 5 | 122 ± 3 |
| Graft recipient* | [c]501 ± 24 | [c]336 ± 33 | [a]207 ± 28 | 109 ± 11 | [a]97 ± 11 | [b]85 ± 8 | [c]80 ± 8 |

Data express means ± SEM of 9 animals per group.
[a]$p < 0.05$, [b]$p < 0.01$, [c]$p < 0.001$ vs normal controls; unpaired students t-test
*Recipients of 1.0 to 1.8 million β cells; for 2/11 fetal pig preparations, no correction of diabetes was observed. Mean survival time of diabetic controls was 11 ± 3 days post alloxan treatment.

What is claimed is:

1. A method for preparing a preparation of mammalian pancreatic endocrine cells comprising:
   dissociating intact pancreatic tissue into a cell suspension comprising single cells and cellular aggregates;
   removing single cell and cellular aggregates larger than 100 μm from said cell suspension;
   enriching said cell suspension with regard to the content in endocrine cells and cellular aggregates with size ≦100 μm; and
   removing contaminating non-endocrine cells by density centrifugation, wherein the resulting preparation of mammalian pancreatic endocrine cells consists essentially of endocrine cells and cellular aggregates having sizes ≦100 μm.

2. The method according to claim 1, wherein said cell suspension is being enriched by separating single cells and cellular aggregates with size <100 μm.

3. The method according to claim 2, wherein said cell suspension is being enriched by separating single cells with size <15 μm.

4. The method according to claim 2, wherein said cell suspension is being enriched by separating cellular aggregates with a size of 15 to 100 μm.

5. The method according to claim 2, wherein said cell suspension is being enriched by counterflow centrifugation or elutriation and wherein said cell suspension is being enriched by separating single cells with a size of 6–15 μm.

6. The method according to claim 2, wherein contaminating acinar cells are removed by density gradient centrifugation using a layer with a density of at least 1.075 g/l.

7. The method as claimed in claim 6, wherein the intact pancreatic tissue is dissociated by sequential shaking incubations, first in the presence of collagenase and second in a calcium-free medium.

8. The method according to claim 7, wherein the separatino comprises centrifugation through a layer with a density <1.05 g/ml in order to enrich in viable cells.

9. The method according to claim 8, wherein said separated cells or aggregates with a size <100 μm are used to further purify beta cells with a mature or immature phenotype, glucagon-containing alpha cells, and/or non-granulated cells containing precursor endocrine cells, by fluorescence activated cell sorting (FACS).

10. The method according to claim 9, wherein immature pancreatic endocrine cells survive, and are further enriched, by suspension culture in serum-free medium containing glucocorticoids and nicotinamide.

11. The method according to claim 10, wherein immature endocrine cells are maintained during culture with serum.

12. The method according to claim 11, wherein the pancreatic tissue is obtained from fetal pig.

13. The method according to claim 12, wherein the fetal pig is obtained from a pregnant sow of minimally 108 days of gestation.

14. The method according to claim 13, wherein the cell suspension depleted in single immature endocrine cells is used to obtain a cell preparation enriched in mature endocrine cells.

15. The method according to claim 1, wherein minimally $10^7$ endocrine cells are isolated per mammalian pancreas at a higher than 80% purity with minimally 40% insulin immunoreactive cells.

16. The method according to claim 15, wherein mammalian beta cell preparations are produced with a potential for growth in vitro and in vivo, following transplantation.

17. The method according to claim 16, wherein mammalian alpha cell preparations are produced at minimally 65% purity.

18. The method according to claim 17, wherein mammalian beta cell preparations can be cultured for minimally four weeks while retaining an insulin biosynthetic activity of more than 10 fmol/$10^3$ beta cells/hr.

19. A preparation of viable endocrine cells obtainable by a method according to claim 11.

20. The preparation according to claim 19, comprising more than 40% insulin containing beta cells.

21. The preparation as claimed in claim 20, for use in the treatment of diabetes mellitus.

* * * * *